(12) United States Patent
Finkelstein

(10) Patent No.: US 6,474,520 B1
(45) Date of Patent: Nov. 5, 2002

(54) REMOVABLY ATTACHABLE CONTAINER HOLDER APPARATUS AND METHOD

(75) Inventor: Susan R. Finkelstein, Austin, TX (US)

(73) Assignee: ASPE, Inc., Austin, TX (US)

( * ) Notice: Subject to any disclaimer, the term of this patent is extended or adjusted under 35 U.S.C. 154(b) by 4 days.

(21) Appl. No.: 09/690,186

(22) Filed: Oct. 16, 2000

(51) Int. Cl.$^7$ ................................................. A45F 5/00
(52) U.S. Cl. .................... 224/267; 224/219; 224/222
(58) Field of Search ............................. 224/267, 148.6, 224/219, 220, 222, 250; D3/229; 128/205.22

(56) References Cited

U.S. PATENT DOCUMENTS

| | | | |
|---|---|---|---|
| 5,446,953 A | * | 9/1995 | LeFeber ..................... 224/222 |
| 5,558,440 A | * | 9/1996 | Miller ........................ 224/219 |
| 5,730,118 A | | 3/1998 | Hermanson |
| 5,732,860 A | * | 3/1998 | Faraj ........................ 224/148.2 |
| 5,755,366 A | * | 5/1998 | Mazzo ....................... 224/222 |
| 5,779,122 A | | 7/1998 | Martinelli |
| 5,820,000 A | * | 10/1998 | Timberlake et al. ......... 224/267 |
| 5,855,307 A | | 1/1999 | Biddick et al. |
| 5,938,089 A | * | 8/1999 | Abreu-Marston ........... 224/267 |
| 5,967,391 A | * | 10/1999 | Hunt .......................... 224/222 |
| 6,325,260 B1 | * | 12/2001 | Gorham ...................... 224/222 |

* cited by examiner

Primary Examiner—Stephen K. Cronin
Assistant Examiner—Maerena W. Brevard
(74) Attorney, Agent, or Firm—J. Nevin Shaffer, Jr.; Shaffer & Culbertson, L.L.P.

(57) ABSTRACT

Removably attachable container holder (10) includes a pressure dispersing conformable pad (12). Pressure dispersing conformable pad (12) includes multiple self-sizing container receivers (18) and a first free end (14) and a second free end (16). Connection straps (20) are connected, one each, to each free end (14) and (16). In a preferred embodiment, hook and loop material (24) is connected to straps (20). Pressure dispersing conformable pad (12) is one width and connection straps (20) and multiple self-sizing container receivers (18) are of another, smaller, a width.

10 Claims, 3 Drawing Sheets

REMOVABLY ATTACHABLE CONTAINER HOLDER APPARATUS AND METHOD

BACKGROUND OF THE INVENTION

This invention relates to an improved removably attachable container holder. In particular, in the field of sports medicine and athletics, this invention relates to an improved removably attachable medicine container holder.

The circumstances wherein individuals find it necessary to carry essential items on their person are many. When faced with such a circumstance, individuals often initially choose the path of least resistance. Wallets, purses, and pockets are often the first choice and suffice in most circumstances. Nonetheless, many circumstances arise wherein wallets, purses and pockets are not satisfactory solutions. Often the thing being carried is too bulky and uncomfortable to use these ordinary locations. Thus, the prior art includes fanny packs, backpacks and the like for adding carrying capacity to an individual. These solutions however are themselves bulky and restricting.

Other solutions known in the prior art include a device disclosed in Martinelli, U.S. Pat. No. 5,779,122, for a pouch with a spring clip to hold the pouch to a user's belt. For casual movements the clip causes no problem. Nonetheless, during strenuous exercise and in situations were no belt is present, for example when jogging, the clip becomes a painful aggravation.

A chain device eliminates the need for a clip as disclosed in Hermanson, U.S. Pat. No. 5,730,118. Here, a chain is connected to a rigid holder for carrying a container and for retaining the container within the holder. Again, this device is satisfactory for casual use but is unsatisfactory in athletic situations. One device of which the inventor is aware is a wrist band for holding an inhaler. Biddick, U.S. Pat. No. 5,855,307 discloses an elastic band with a container holder attached perpendicularly to the band. The container holder retains the container in such a way that when the user's wrist is brought up to the user's mouth the container, such as an inhaler, is in an upright position for use.

As is often the case, the item being carried frequently must be carried in a certain position, such as one end up. Additionally, in most circumstances it is desirable that the thing being carried be carried in such a way as to not add to the user's overall fatigue. Even a small amount of weight added to a user's wrist, for example, multiplies the weight of the device and, over time, greatly increases fatigue. Additionally, it is most often the case that whatever it is that is being carried must be easily accessible and removable from the carrying device for proper use. Any carrying device from which the desired container is not freely and easily detachable greatly diminishes its usefulness. Further, the carrying device must not be unduly constrictive when in use.

Thus, there is a need in the art for a removably attachable container holder that is easy-to-use, light weight and which is not unduly constrictive when in use. Further, there is a need in the art for a removably attachable container holder from which the container is easily removed and replaced and which holds the container in a desired position. It, therefore, is an object of this invention to provide an improved removably attachable container holder that does not add fatiguing, bulky, constricting objects to a user and which, in fact, disperses attachment pressure when in use.

SHORT STATEMENT OF THE INVENTION

Accordingly, the removably attachable container holder of the present invention includes a pressure dispersing conformable pad of one certain width with two free ends. Multiple self-sizing container receivers, of a second smaller width, are connected to the pressure dispersing conformable pad. A pair of connection straps, also of the second smaller width, are connected to the pressure dispersing conformable pad, one connection strap attached to each free end. In a preferred embodiment the pressure dispersing conformable pad width is half again as wide as the second smaller width. In another preferred embodiment, the container receivers are parallel to the pressure dispersing conformable pad. In other preferred embodiments the container receivers are formed of elastic material that resists expansion and the container receivers and the connection straps are integrally formed from a single piece of the elastic material attached to the pressure dispersing conformable pad. In still other preferred embodiments, the invention includes at least two container receivers and the pressure dispersing conformable pad has an inside and an outside and one connection strap is connected to the outside and one connection strap is connected to the inside.

In other preferred embodiments, the pressure dispersing conformable pad is one-quarter inch neoprene and the connection straps include opposing hook and loop material. In a still further preferred embodiment, the hook and loop material covers a portion of the pressure dispersing conformable pad. Additionally, a method of providing a removably attachable container holder is disclosed and claimed more fully hereafter.

BRIEF DESCRIPTION OF THE DRAWINGS

Other objects, features and advantages of the present invention will become more fully apparent from the following detailed description of the preferred embodiments, the appended claims and the accompanying drawings in which:

DETAILED DESCRIPTION OF THE PREFERRED EMBODIMENTS

Figure 1:
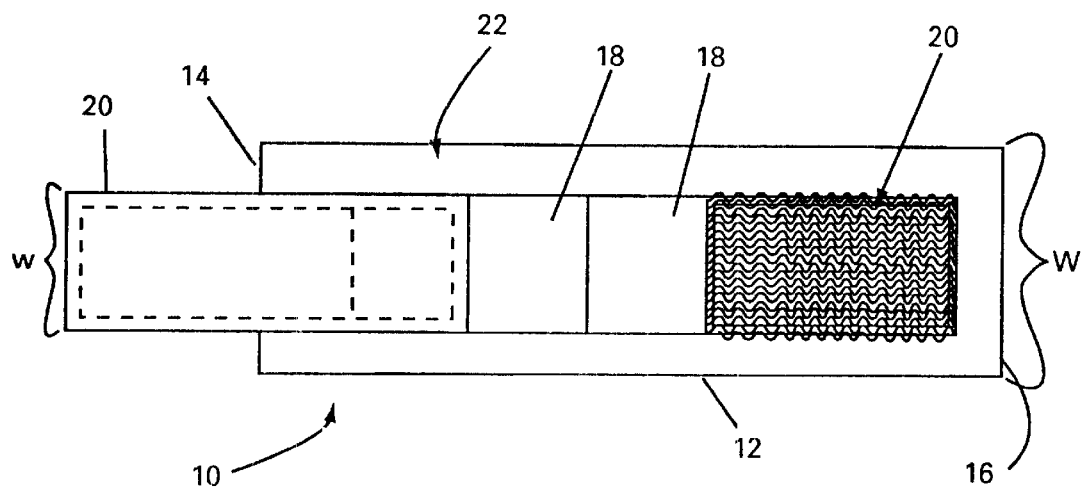
FIG. 1 is a top view of the outside of a preferred embodiment of the removably attachable container holder of the present invention.

The preferred embodiments of the present invention are illustrated by way of example in FIGS. 1–5. With specific reference to FIGS. 1 and 2, removably attachable container holder 10 includes pressure dispersing conformable pad 12. Pressure dispersing conformable pad 12 has a first free end 14 and a second free end 16. Additionally, pressure dispersing conformable pad 12 has a certain width "W".

Multiple self-sizing container receivers 18 are connected to pressure dispersing conformable pad 12. Self-sizing container receivers 18 have a certain, smaller, width "w". A pair of connection straps 20, also of smaller width "w", are attached one each to free ends 14 and 16.

In a preferred embodiment, connection straps 20 are attached to the top 22 of pressure dispersing conformable pad 12. Further, in a preferred embodiment, hook and loop material 24 is connected to a portion of the connection straps 20 on the top 22 of pressure dispersing conformable pad 12.

Figure 2:
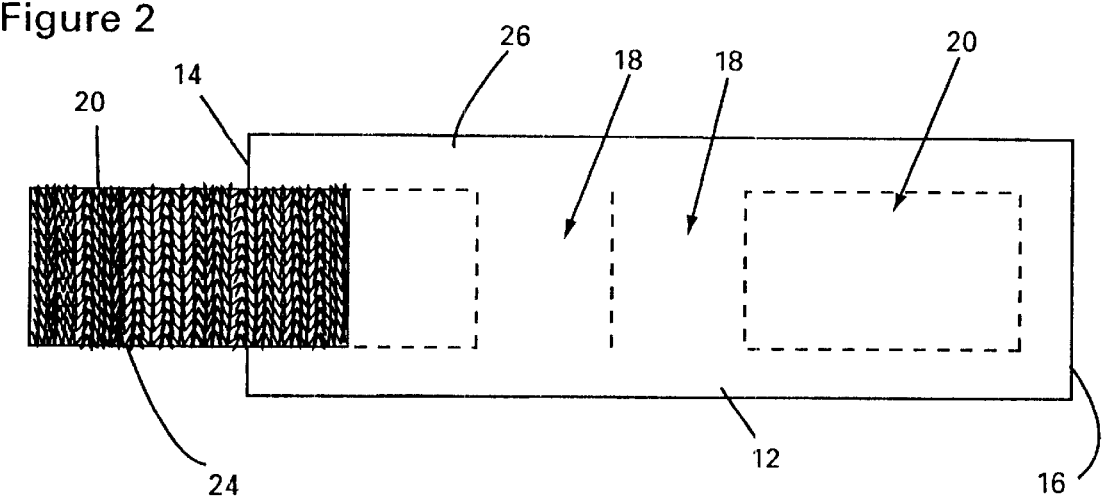
FIG. 2 is a bottom view of the inside of the invention of FIG. 1.

Referring now to FIG. 2, the bottom 26 of pressure dispersing conformable pad 12 is displayed. In a preferred embodiment, the hook and loop material 24 is attached to one of the connection straps 20 on the bottom 26 of pressure dispersing conformable pad 12. FIG. 2 also illustrates a preferred embodiment wherein hook and loop material 24 not only covers connection strap 20 but also covers some portion of the bottom 26 of pressure dispersing conformable pad 12.

Both FIGS. 1 and 2 illustrate a unique feature of the present invention, wherein pressure dispersing conformable pad is much wider than multiple self-sizing container receivers 18 and the pair of connection straps 20.

Figure 3:
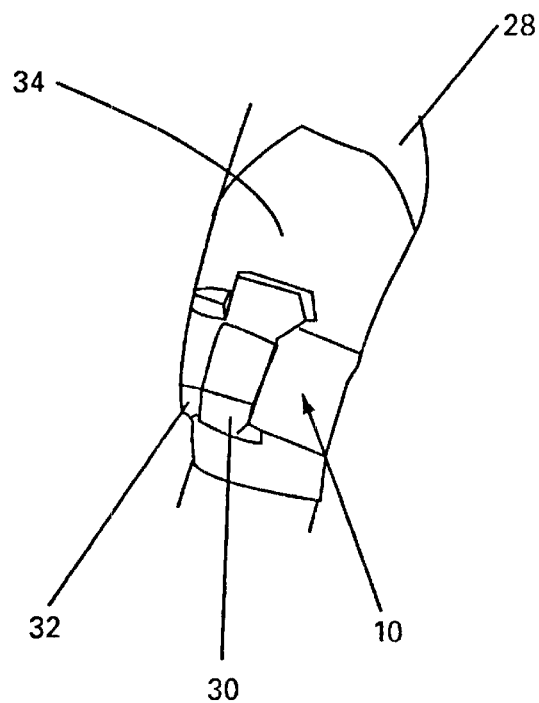
FIG. 3 is a perspective view of the invention of FIG. 1 shown attached to a runner's upper arm.
Figure 4:
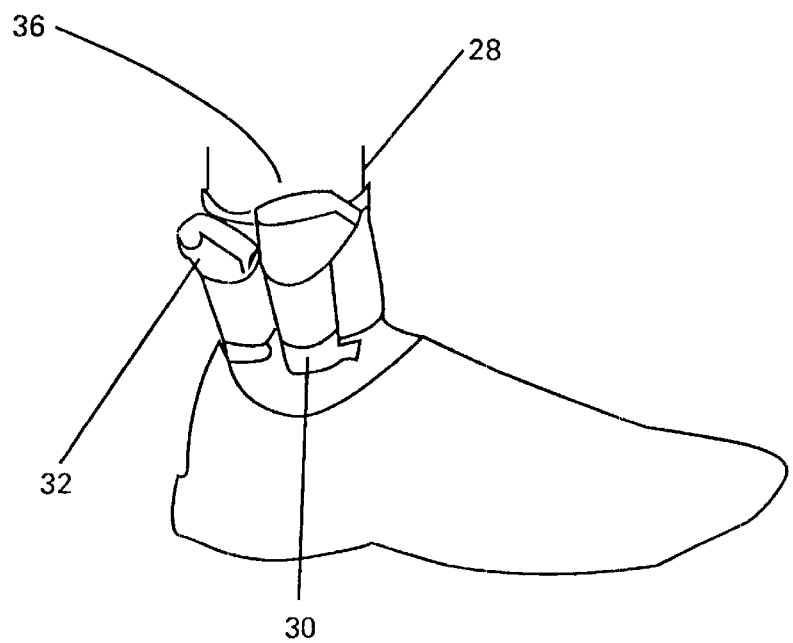
FIG. 4 is a perspective view of the invention of FIG. 1 shown attached to a runner's lower leg.
Figure 5:
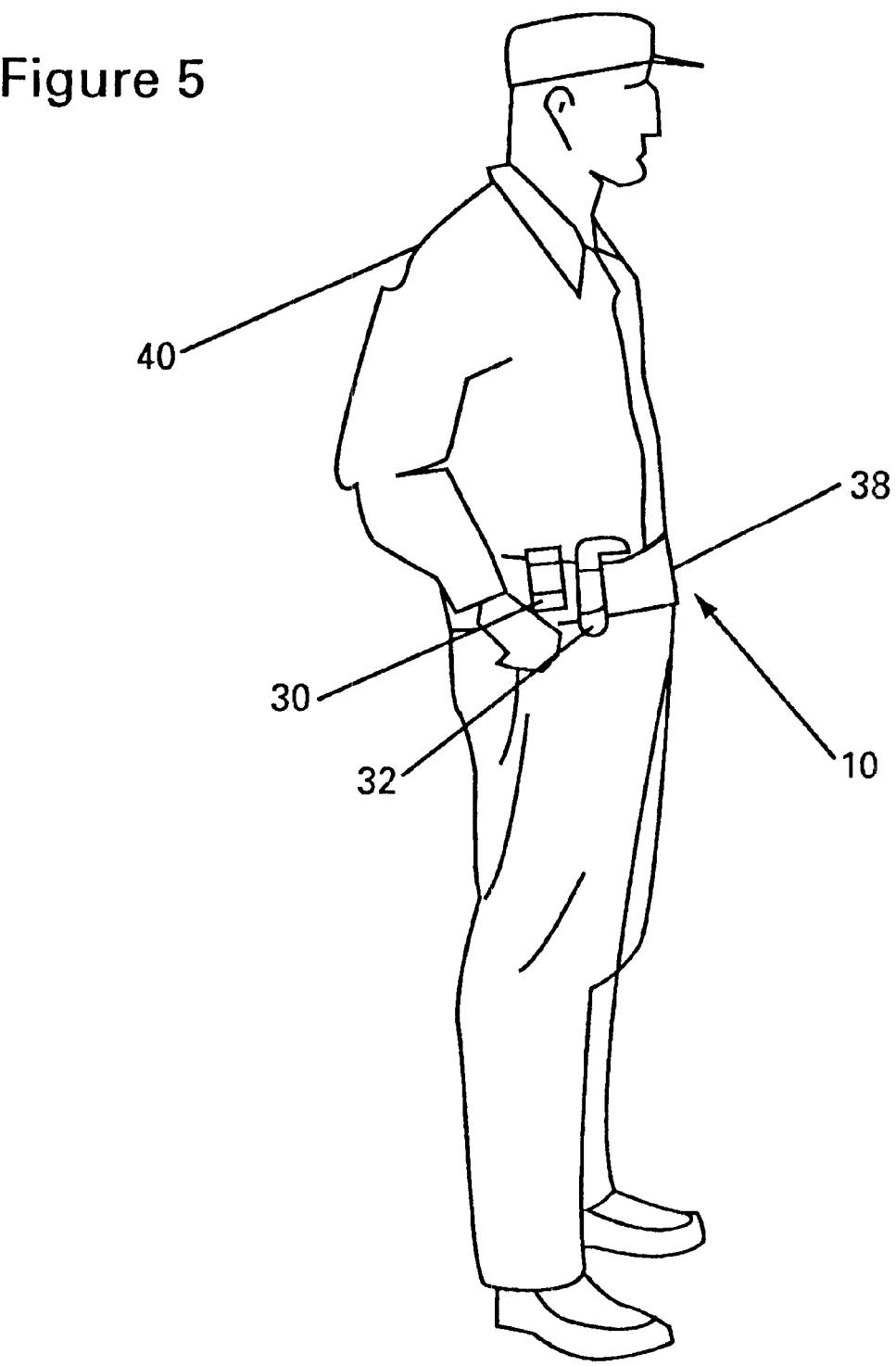
FIG. 5 is a perspective view of the invention of FIG. 1 shown attached to a runner's waist.

The removably attachable container holder 10 of the present invention is useful in a wide variety of circumstances. In each of the circumstances, the benefits of the invention are manifest. Referring to FIGS. 3, 4 and 5, multiple applications and benefits of the invention are illustrated. Among those benefits are the ease with which removably attachable container holder 10 is attached to a user 28; the fact that multiple containers, container 30 and container 32, are held in an upright position; the fact that container 30 and container 32 are easily removed from multiple self-sizing container receivers 18; and the fact that pressure dispersing conformable pad 12 effectively disperses the attachment pressure thereby making its use more comfortable and non-fatiguing.

Referring now to FIG. 3, the use of removably attachable container holder 10 is shown being worn by user 28 attached to the user's 28 arm 34. Importantly, containers 30 and 32 are held in the required upright position when not needed and are easily removed from self-sizing container receivers 18 when needed. Additionally, removably attachable container holder 10 does not add significantly to the weight of containers 30 and 32 and thereby does not add appreciably to the user's 28 fatigue levels.

Referring to FIG. 4, removably attachable container holder 10 is shown attached to a user's 28 lower leg 36. Once again the advantages of applicant's invention are apparent. Pressure dispersing conformable pad 12 not only dispenses the attachment pressure, but also shields a user's 28 leg 36 from shock transmitted from containers 30 and 32 during running or jogging, for example.

Referring now to FIG. 5, removably attachable container holder 10 is shown attached to user's 28 waist 38. In this location, applicant's invention serves also to support a user's 28 back 40. In this embodiment, removably attachable container holder 10 may have a width sufficiently wide to cover a large area of a user's 28 back 40 and serve the function of a mild back support as well as a container holder.

In use, pressure dispersing conformable pad 12 is formed in a certain width with two free ends 14 and 16. In a preferred embodiment, pressure dispersing conformable pad 12 is formed from ¼ inch thick neoprene. The thickness of the neoprene is a matter of design choice. Nonetheless, the thickness of the pad must be thick enough to allow pressure dispersing conformable pad 12 to sufficiently insulate containers 30 and 32 from user 28 and sufficiently wide enough to allow attachment pressure to be dispersed. Certainly any flexible conformable resilient pad material is suitable.

In a preferred embodiment, pressure dispersing conformable pad 12 is half again as wide ("W") as the second smaller width ("w") of connection straps 20 and container receivers 18. Another preferred embodiment has multiple self-sizing container receivers 18 located parallel to pressure dispersing conformable pad 12. In another preferred embodiment multiple self-sizing container receivers 18 are formed of an elastic material that resists expansion. Any now known or hereafter discovered material is suitable that is stretchable and which tends to return to its unstretched form after use.

In further preferred embodiments, at least two, or only two, self-sizing container receivers 18 are formed. In still further preferred embodiments, pressure dispersing conformable pad 12 has an outside or bottom 26 and an inside or top 22 with one connection strap 20 connected to the outside 26 and one connection strap 20 connected to the inside 22. In another embodiment, hook and loop material 24 is utilized, as illustrated in the figures, with connection straps 20. Certainly, any means of joining connection straps 20 together that is easy to use and light weight is appropriate as well. In one embodiment, as illustrated in FIG. 2, hook and loop material 24 covers a portion of pressure dispersing conformable pad 12 so that should a user's 28 arm 34 be small, removably attachable container holder 10 can still be utilized.

In the field of sports medicine, the use of removably attachable container holder 10 is primarily with the use of medicines such as contained in inhalers, for example. Nonetheless, any needed item may be easily attached to and removed from multiple self-sizing container receivers 18.

While the present invention has been disclosed in connection with the preferred embodiments thereof, it should be understood that there may be other embodiments which fall within the spirit and scope of the invention as defined by the following claims.

I claim:

1. A removably attachable container holder comprising:
    (a) a pressure dispersing conformable pad of one certain width with two free ends;
    (b) multiple self-sizing container receivers of a second smaller width connected to said pressure dispersing conformable pad;
    (c) a pair of connection straps of said second smaller width for connection to each other for securing said pressure dispersing conformable pad in a selected place, wherein one connection strap is attached to each free end of said pressure dispersing conformable pad; and
    (d) wherein said container receivers and said connection straps are integrally formed from a single piece of elastic material attached to said pressure dispersing conformable pad.

2. The invention of claim 1 wherein said pressure dispersing conformable pad width is twice as wide as said second smaller width.

3. The invention of claim 1 wherein said container receivers are parallel to said pressure dispersing conformable pad.

4. The invention of claim 1 wherein said container receivers are formed of elastic material.

5. The invention of claim 1 further comprising at least two self-sizing container receivers.

6. The invention of claim 1 further comprising two self-sizing container receivers.

7. The invention of claim 1 wherein said pressure dispersing conformable pad has an inside and an outside and one connection strap is connected to said outside and one connection strap is connected to said inside.

8. The invention of claim 1 wherein said pressure dispersing conformable pad is one-quarter inch neoprene.

9. The invention of claim 1 wherein said connection straps include opposing hook and loop material.

10. The invention of claim 9 wherein said hook and loop material covers a portion of said pressure dispersing conformable pad.

* * * * *